(12) United States Patent
Terakura et al.

(10) Patent No.: US 7,245,377 B2
(45) Date of Patent: Jul. 17, 2007

(54) COLORIMETRY DEVICE

(75) Inventors: Naoyuki Terakura, Kanagawa (JP); Yasuyoshi Ota, Kanagawa (JP)

(73) Assignee: Yokohama Electric Communications & Solutions Co., Ltd., Kanagawa (JP)

( * ) Notice: Subject to any disclaimer, the term of this patent is extended or adjusted under 35 U.S.C. 154(b) by 175 days.

(21) Appl. No.: 11/076,919

(22) Filed: Mar. 11, 2005

(65) Prior Publication Data
US 2006/0007443 A1    Jan. 12, 2006

(30) Foreign Application Priority Data
Jul. 8, 2004    (JP) .............................. 2004-201304

(51) Int. Cl.
*G01N 21/86* (2006.01)
*G01N 21/27* (2006.01)

(52) U.S. Cl. .................. 356/402; 356/425; 356/419
(58) Field of Classification Search ......... 356/402–425
See application file for complete search history.

(56) References Cited
U.S. PATENT DOCUMENTS

| | | | | |
|---|---|---|---|---|
| 3,885,878 | A | * 5/1975 | Ishak ....................... | 356/405 |
| 4,029,419 | A | * 6/1977 | Schumann et al. ......... | 356/402 |
| 4,033,698 | A | * 7/1977 | Demsky et al. ............ | 356/402 |
| 4,380,169 | A | 4/1983 | Graham | |
| 4,715,715 | A | * 12/1987 | Howarth et al. ............ | 356/402 |
| 4,950,905 | A | * 8/1990 | Butler et al. ............. | 250/358.1 |

FOREIGN PATENT DOCUMENTS

| | | |
|---|---|---|
| JP | S63-155032 U | 10/1988 |
| JP | S64-049933 A | 2/1989 |
| JP | H06-011442 A | 1/1994 |
| JP | H08-114503 A | 5/1996 |
| JP | H08-327538 A | 12/1996 |
| JP | H09-152400 A | 6/1997 |
| JP | H09/218159 A | 8/1997 |
| JP | 2001-174966 A | 6/2001 |
| JP | 2002-117402 A | 4/2002 |
| WO | WO 02/052249 A1 | 7/2002 |

\* cited by examiner

*Primary Examiner*—Akm Ullah
*Assistant Examiner*—Rebecca C. Slomski
(74) *Attorney, Agent, or Firm*—Sughrue Mion, PLLC

(57) ABSTRACT

A colorimetry device having a light source for irradiating light to a measured object, a cover part provided with a take-out port for taking out light diffused from the measured object, and a placing part on which the measured object is placed, the measured object being put between the cover part and the placing part, so as to effect the color measurement of the measured object. A hinge mechanism is provided, so that when the measured object is placed on the placing part and the cover part is in a closed state, a measurement space dividing section for defining a measurement space between the cover part and the placing part is provided. A measuring light may also be arranged to irradiate the rear face of the measured object.

6 Claims, 5 Drawing Sheets

COLORIMETRY DEVICE

BACKGROUND OF THE INVENTION

1. Field of the Invention

The present invention relates to a colorimetry device, and more particularly to a colorimetry device for performing color analysis of a leaf of a plant and the like.

2. Description of the Prior Art

With the progress of the biotechnology, there has been a demand for a colorimetry device for performing color analysis of a leaf of a plant, and the like. As examples of the colorimetry devices, there are well known in the art a device using an integrating sphere (see patent documents 1, 2), and the 0/45 geometry (an measurement geometry in which a measured object is irradiated with measuring light at a right angle (0 degree) so as to enable light diffused therefrom to be detected by a light receiving element arranged at an angle of 45 degrees relative to the irradiation light), and the like. A technique for analyzing a vegetation state of a plant is also disclosed in the patent document 3.

Patent document 1: Japanese Patent Laid-Open No. 8-114503

Patent document 2: Japanese Patent Laid-Open No. 9-218159

Patent document 3: Japanese Patent Laid-Open No. 2002-117402

In a device using the integrating sphere and a device using the 0/45 geometry disclosed in the above described patent documents 1, 2, a leaf of a plant, which is a measured object, needs to be collected and made to be fetched to such devices installed in a study room and a laboratory so as to be measured. However, there is a demand for measuring color of a leaf, etc. in a state that a plant is actually planted in the field (without the leaf being cut off from the plant).

Although the technique for analyzing vegetation state of a plant is disclosed in the patent document 3, the technique is intended for performing color analysis based on a picture taken from the sky, making it impossible to perform color measurement of individual leaves of plants at a site.

BRIEF SUMMARY OF THE INVENTION

An object of the present invention is to provide a colorimetry device which in the case of measuring color of a leaf of a plant, etc., enables the measurement to be performed while leaving the plant as it is without the leaf to be measured cut off and the plant being damaged.

According to the present invention, there is provided a colorimetry device for measuring color of a measured object, which comprises: a first member provided with a light source for irradiating the measured object with light, and a take-out port for taking out light diffused from the measured object; and a second member on which the measured object is placed, and which enables color measurement of the measured object to be performed by putting the measured object between the first and second members.

Further, the colorimetry device is characterized in that the device comprises a light source provided for the second member, for irradiating the measured object with light, and in that the ratio of the light quantity of the light source provided for the said second member to the light quantity of the light source provided for the first member is set in a range of about 20 to 60%.

Further, the colorimetry device is characterized in that the device comprises a connecting member for connecting the first and second members in an openable and closable manner, and a measurement space dividing section for defining a measurement space between the first and second members when the first and the second members are made to be in a closed state by the connecting member.

Further, the colorimetry device is characterized in that the device comprises means for correcting the effect of external light leaking through a contact part between the measured object and the measurement space dividing section, and in that the means is adapted to correct the effect on an output from the take-out port when the light source is turned on, by using an output from the take-out port when the light source is turned off. Further, the colorimetry device is characterized in that the device comprises first means for detecting an output from the take-out port when the light source is turned on, second means for detecting an output from the take-out port when the light source is turned off and means for subtracting the output detected by the second means from the output detected by the first means.

The operation of the present invention will be described below. According to the present invention, a first member provided with a light source for irradiating light to a measured object and with a take-out port for taking out light diffused from the measured object, and a second member on which the measured object is placed, are provided so that the measured object is put between both the members so as to enable the color measurement to be performed. In this case, both the members are configured to be connected with each other in an openable and closable manner, so that when the measured object such as a leaf is placed on the second member and the first member is made to be in a closed state, the measurement space dividing section for defining a measurement space can be provided between both the members.

Since a gap is formed in a contact part between the measurement space dividing section and the measured object at this time, making it impossible to prevent external light from leaking from the outside, a function of correcting the effect of the external light is provided. This makes it possible to measure color of a leaf of a plant, etc. as it is without cutting off the leaf to be measured and damaging the plant at the time of the measurement.

Further, in addition to the light source provided for the first member, another light source is also provided for the second member, so as to irradiate light from both front and rear faces of the measured object. Since light transmitted from the rear surface of the measured object such as a leaf is present in the nature in addition to light irradiated to the object, another light source is provided in order to create an environment closer to the nature, i.e. an environment closer to the visual measurement, thereby enabling color measurement to be performed by taking the light transmitted through the measured object into consideration as well.

DETAILED DESCRIPTION OF THE PREFERRED EMBODIMENTS

Figure 1:
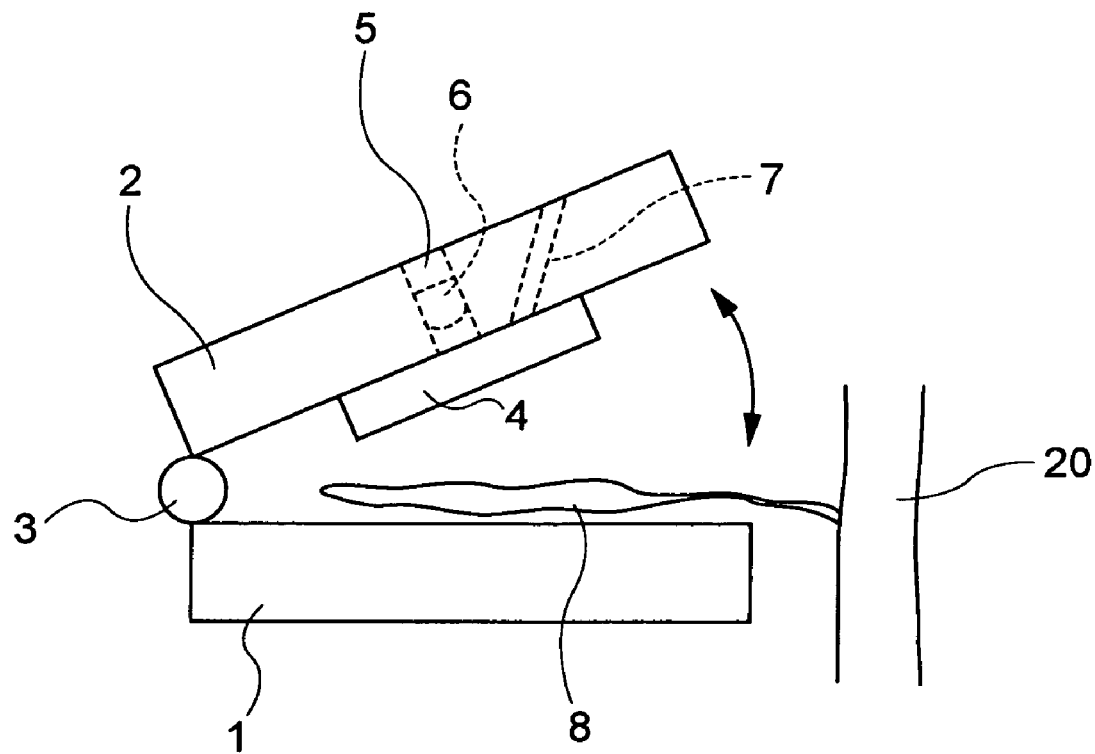
FIG. 1 is a front view of a first embodiment according to the present invention, in which a placing part 1 and a cover part 2 are in an opened state.
Figure 2:
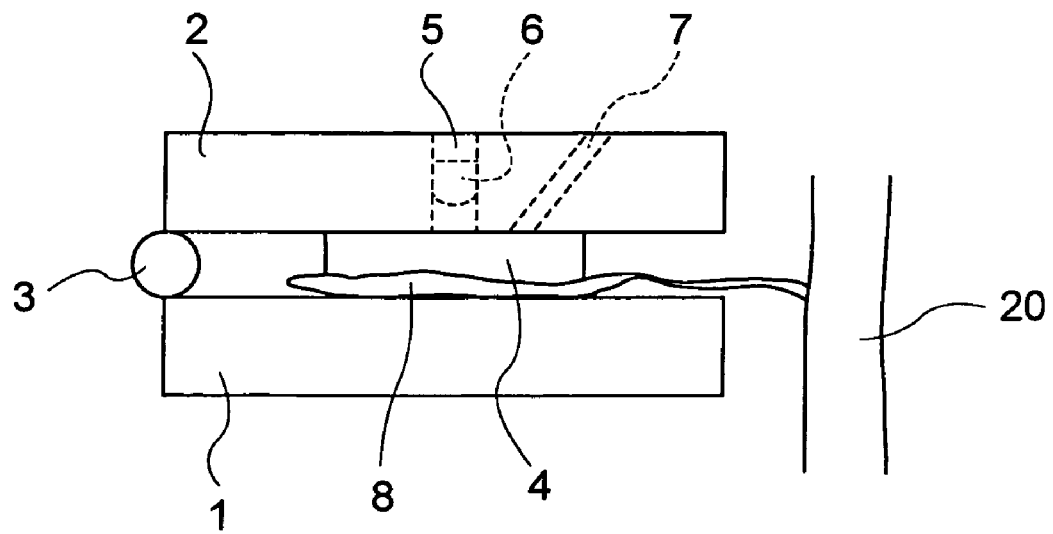
FIG. 2 is a front view of the embodiment according to the present invention, in which the placing part 1 and the cover part 2 are in a closed state.
Figure 3:
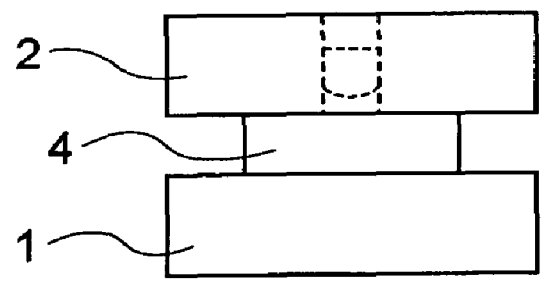
FIG. 3 is a side view of the first embodiment according to the present invention.
Figure 4:
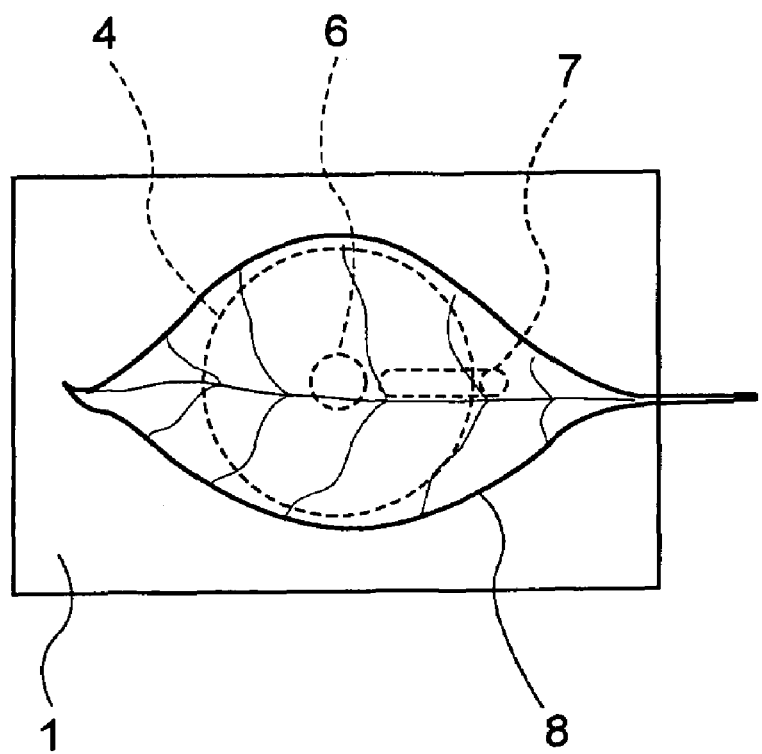
FIG. 4 is a top view in FIG. 2, and is a perspective illustration of the cover part.

Embodiments according to the present invention will be described in more detail hereinbelow, with reference to the accompanying drawings. FIGS. 1 and 2 are front views showing an embodiment according to the present invention, and FIG. 3 is the side view of the embodiment. FIG. 1 is a figure in the case where the placing part 1 on which a leaf 8 which is a measured object is placed, and a cover part 2 are in an opened state, and FIG. 2 is a figure in the case where they are in a closed state. FIG. 4 is also a figure in the case where the cover part 2 is seen through from the top surface in the state in FIG. 2, and the equivalent parts are denoted by the same reference numerals in FIGS. 1 to 4.

Referring now to the figures, a leaf 8 which is a measured object is placed on the placing part 1. The placing part 1 and the cover part 2 are connected by a hinge mechanism 3 in an openable and closable manner. The cover part 2 is provided with a measuring light source 6 for irradiating light having a fixed spectral characteristic and light quantity to the leaf 8, and with a diffused light take-out port 7 for detecting light diffused from the leaf 8. The measuring light source 6 irradiates light at right angles to the leaf 8, and the diffused light take-out port 7 is formed in the cover part 2 at an angle of 45 degrees to the measuring light source 6, thereby constituting a so-called 0/45 geometry. Also, reference numeral 5 denotes a measuring light source mounting hole.

As shown in FIG. 2, in order to define a measurement space for measuring color of the leaf 8 when the placing part 1 and the cover part 2 are in a closed state, the cover part 2 is provided with a measurement space dividing section 4. The leaf 8 of a plant 20 is placed on the placing part 1 and the cover part 2 is rotated about the hinge mechanism 3, so as to enable the leaf 8 to be put between the placing part 1 and the cover part 2. At this time, a measurement space is formed by the top surface of the leaf 8 and the measurement space dividing section 4, so that diffused light is diffused in the measurement space when the measuring light source 6 is turned on to irradiate measuring light to the leaf 8. The diffused light is arranged to be taken out from the diffused light take-out port 7 using an optical fiber (not shown), so as to be supplied to a color measuring function section shown in FIG. 5.

Figure 5:
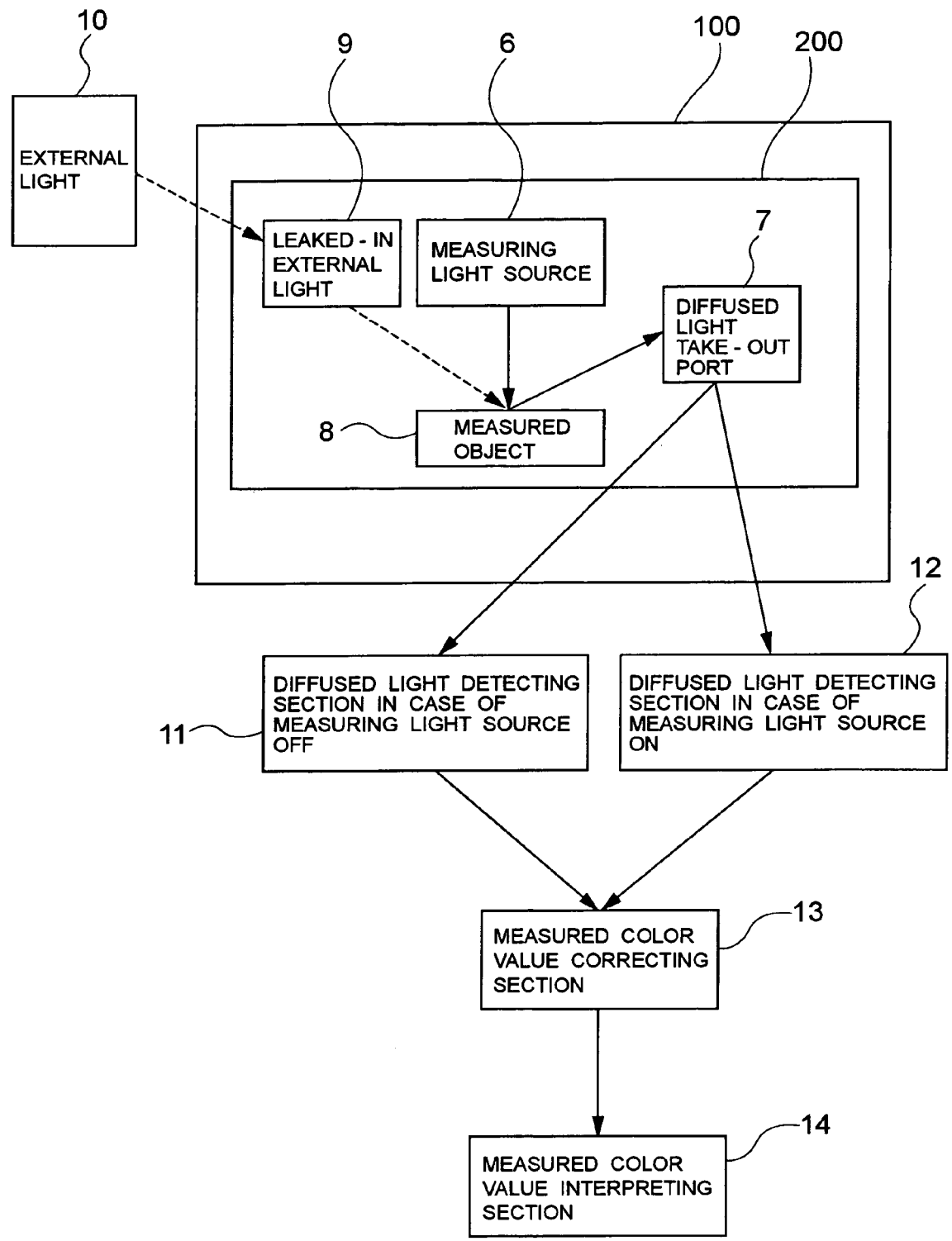
FIG. 5 is a functional block diagram showing the whole configuration of a colorimetry device according to the embodiment of the present invention.

Referring to FIG. 5, a functional block diagram of the embodiment according to the present invention is shown, in which identical parts are denoted by the same reference numerals. In FIG. 5, reference numeral 200 denotes a measurement space which is formed by the placing part 1, the cover part 2 and the measurement space dividing section 4, and reference numeral 100 integrally denotes the members 1, 2, 4 which define the measurement space 200. In this case, external light inevitably leaks in the measurement space 200 through portions of contact of the measured object with the measurement space dividing section 4 and with the placing part 1. In FIG. 5, such light is shown as leaked-in external light 9.

Thus, in the present invention, a function of correcting the effect of the leaked-in external light 9 is also added. That is, light led out from the diffused light take-out port 7 through the optical fiber (not shown) is inputted to a diffused light detecting section 11 in case of the measuring light source OFF, and to a diffused light detecting section 12 in case of the measuring light source ON. Outputs of the diffused light detecting sections 11, 12 are inputted to a measured color value correcting section 13. A correction output from the measured color value correcting section 13 is supplied to a measured color value interpreting section 14, so that color measurement is performed.

In such configuration, first, the measurement space 200 is filled with the leaked-in external light 9 leaked from the contact surface with the measured object 8, etc. when the measuring light source 6 is turned off. Although the leakage of external light 10 to the measurement surface side of the measured object 8 is made to be suppressed by the members 100 (the placing part 1, the cover part 2, the measurement space dividing section 4) for defining the measurement space because the leaked-in external light 9 causes a measurement error, it is impossible to completely suppress such leakage of light. A part of the leaked-in external light 9 in this case is taken out from the diffused light take-out port 7 by means of the optical fiber, and inputted into the diffused light detecting section 11 in case of the measuring light source OFF, so that the quantity of the light is detected. The detected light quantity is assumed to be detected for each RGB (three primary colors).

Next, the same detection processing as that describe above is performed in the state that the measuring light source 6 is turned on. When the measuring light source 6 is turned on, the measurement space 200 is filled with the diffused light which is formed with the leaked-in external light 9 leaked from the contact surface with the measured object 8, etc. and the light from the measuring light source 6, being diffused and reflected by the measured object 8.

A part of the leaked-in external light 9 and the diffused light are taken out from the diffused light take-out port 7, and is inputted via the optical fiber (not shown) into the diffused light detecting section 12 in case of the measuring light source ON, so that the light quantity is detected for each RGB.

In the measured color value correcting section 13, the detection value of the diffused light detecting section 12 in case of the measuring light source ON is corrected for each RGB by the detection value of the diffused light detecting section 11 in case of the measuring light source OFF. As such correcting method, a method of subtraction processing for subtracting the diffused light detection value in case of the measuring light source OFF from the diffused light detection value in case of the measuring light source ON may be used, but a method depending on a statistical processing may also be used. The corrected measured value is inputted into the measured color value interpreting section 14. The measured color value interpreting section 14 has for example, color of leaf measured value interpreting function, and has a function of automatically calculating color information such as a color name and a color code by referring to a color table such as a correspondence table associating codes in the Munsell color system and in PCCS (Practical Color Coordinate System) with RGB values.

Figure 6:
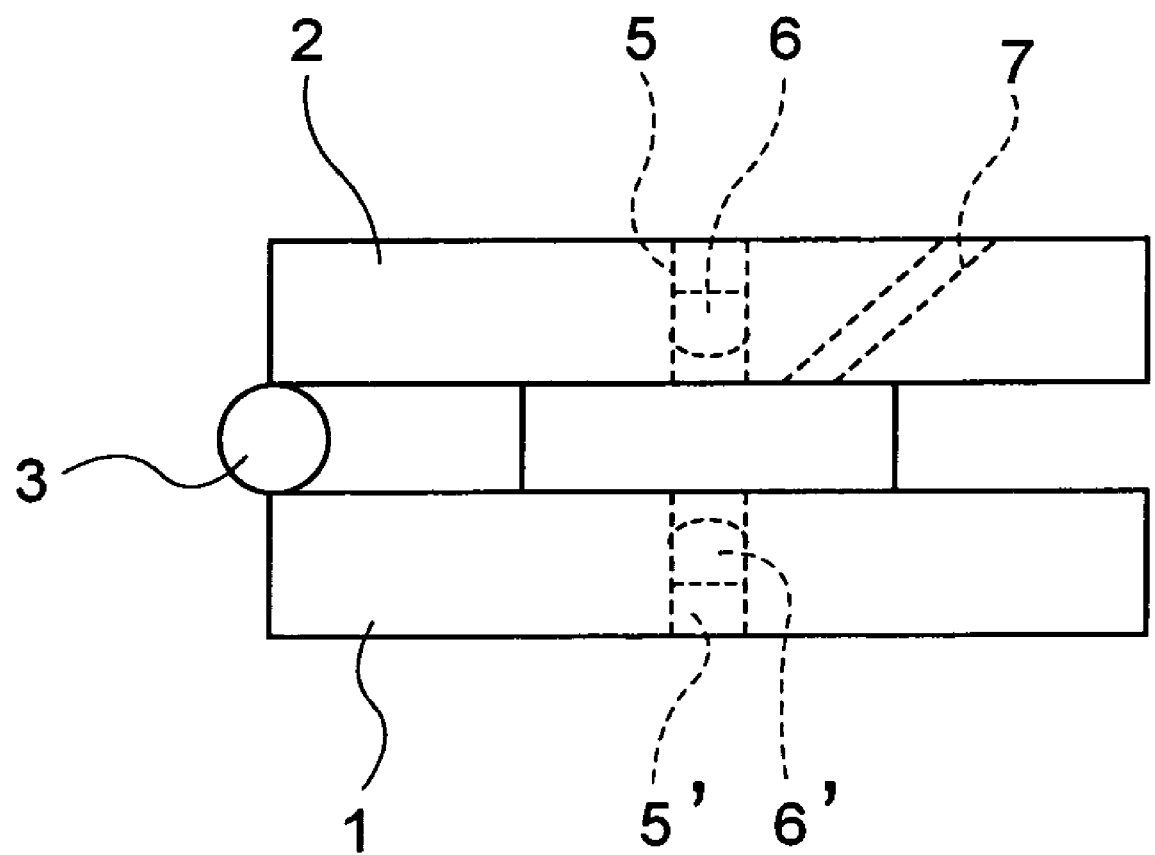
FIG. 6 is a front view of another embodiment according to the present invention, in which the placing part 1 and the cover part 2 are in a closed state.

FIG. 6 is a front view showing a second embodiment according to the present invention, in which parts identical to those in FIGS. 1 to 4 are denoted by the same reference numerals. In this embodiment, measuring light is also arranged to be irradiated from the rear face of the measured object, so that the placing part 1 is also provided with a light source 6' for irradiating light at right angles to the measured object. Reference numeral 5' also denotes a light source mounting hole. Thereby, light transmitted through the measured object can be detected, enabling a more exact color measurement to be performed in consideration of the transmittance of the measured object.

Figure 7A:
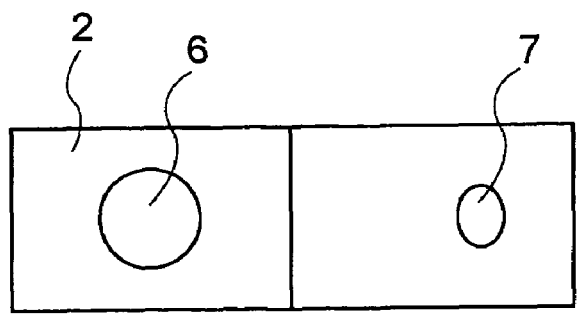
FIG. 7 is a figure showing still another embodiment according to the present invention, in which 7A is a top view and 7B is a front view.
Figure 7B:
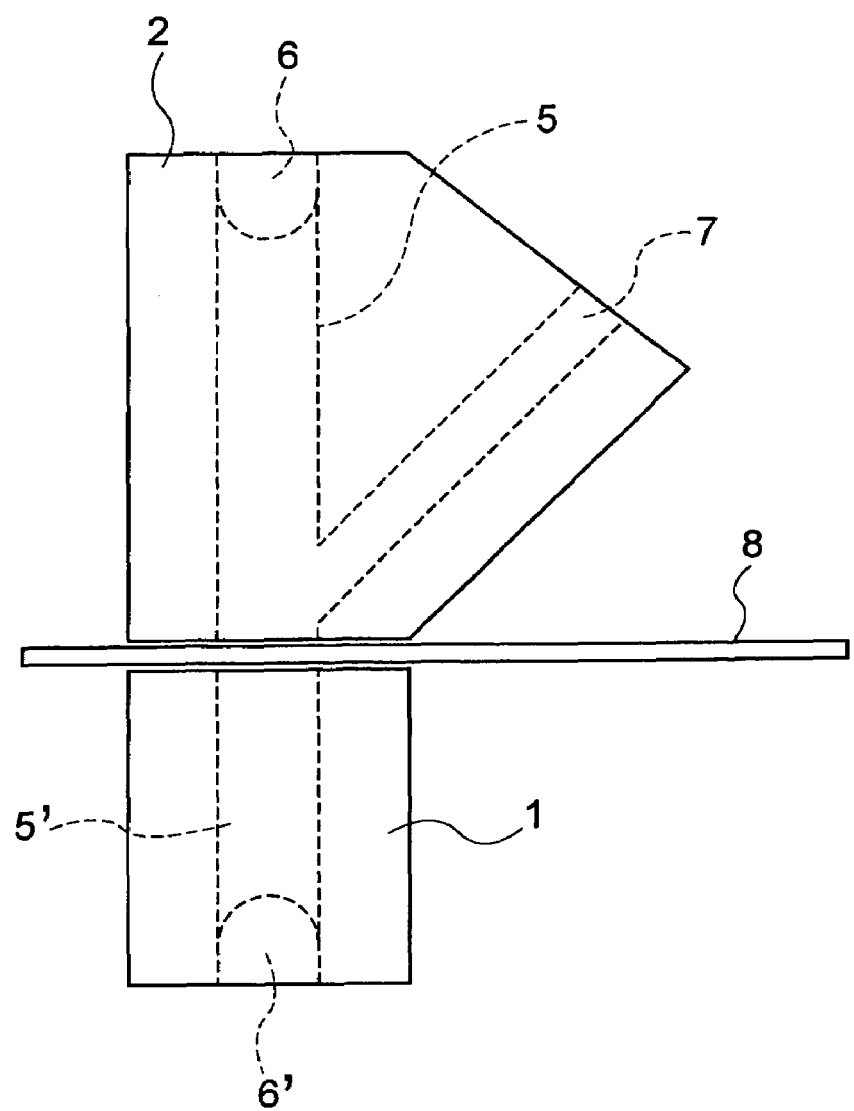

FIG. 7 is a figure showing a third embodiment according to the present invention, in which 7A is a top view and 7B is a front view. In FIG. 7, parts identical to those in FIG. 6 are denoted by the same reference numerals. In this embodiment, light is arranged to be irradiated from both sides of the measured object 8 as in FIG. 6, but measurement is performed by putting the measured object 8 directly between an upper member 2 (corresponding to the cover part in FIG. 6), and a lower member 1 (corresponding to the placing part in FIG. 6). In this case, both of the members 1, 2 may be configured such that they are connected by a connecting member (not shown in particular) so as to be slidable in the vertical direction with respect to each other, but the configuration is not limited thereto.

In the embodiments in FIGS. 6 and 7, light from the light source 6 of the upper member 2 is reflected by the measured object and only the diffuse reflection light is incident on the diffused light take-out port 7 (the specular reflection light is eliminated). Also, light from the light source 6' of the lower member 1 is transmitted through the measured object 8, and only the diffuse transmission light is incident on the diffused light take-out port 7 (light transmitted without being diffused is eliminated). Accordingly, the diffuse reflection light and the diffuse transmission light are added so as to be led out from the diffused light take-out port 7, thereby enabling a measurement condition in consideration of the transmittance of the measured object to be achieved.

Specifically, the ratio of the quantities of light irradiated by both the light sources in the vicinity of the measured object 8 is preferably set so as to agree with a measuring condition during visual color measurement. As an example, the ratio of the light quantity of the light source 6' to the light quantity of the light source 6 is preferably set in a range of about 20 to 60%, and optimally set to be about 40%. An example of the condition of such visual measurement is presented by a color chart of the RHS (The Royal Horticultural Society).

In the above described embodiments, the optical fiber is provided for the diffused light take-out port 7, but an optical sensor (light receiving element) may also be directly provided for the take-out port 7 so as to introduce the light as an electric signal to the outside. Further, the leaf of the plant is used as the measured object, but the measured object is not limited thereto. Further, a configuration of the 0/45 geometry is shown in the above described embodiments, but a configuration of a so-called 45/0 geometry in which the positions of the measuring light source 6 and the diffused light take-out port 7 are reversed, may obviously be adopted as well.

Each of the sections 11 to 14 provided in the exterior of the measurement space 200 shown in FIG. 5, is configured as a computer (information processing device) and the operation procedure is incorporated in the computer as a program beforehand, whereby the function parts can be miniaturized and reduced in weight. The portable colorimetry device can be obtained by connecting the mechanism part for sandwiching the measured object shown in FIGS. 1 to 3 and FIGS. 6, 7, with the computer via an optical fiber and a signal line (for on-off control of the measuring light source).

In addition, the material of the upper member 2 and the lower member 1 may be a metal such as aluminum which can be easily processed, but the material is not limited thereto, and may be other materials which do not transmit light.

According to the present invention, the measured object is arranged to be sandwiched so as to enable color measurement to be performed, so that an effect can be obtained which makes it possible to measure a leaf, etc., which is the measured object, as it is, without the leaf being cut off and the plant being damaged. Further, an effect can be obtained for enabling an accurate color measurement to be performed by adding a function of correcting the effect of external light leaking from the contact part with the measured object. Further, an effect can also be obtained for enabling an accurate color measurement to be performed in consideration of transmitted light by irradiating light from the rear face of the measured object.

What is claimed is:

1. A colorimetry device for measuring color of a measured object, comprising:
   a first member provided with a light source for irradiating light to the measured object, and a take-out port for taking out light diffused from said measured object;
   a second member on which said measured object is placed; and a light source provided for said second member, for irradiating light to said measured object,
   wherein said measured object being put between said first and second members for effecting color measurement of said measured object.

2. The colorimetry device according to claim 1, wherein a ratio of light quantity of the light source provided for said second member to light quantity of the light source provided for said first member is set in a range of about 20 to 60%.

3. The colorimetry device according to claim 1, further comprising: a connecting member for connecting said first and second members in an openable and closable manner; and a measurement space dividing section for defining a measurement space between said first and second members when the first and second members are made to be in a closed state by said connecting member.

4. The colorimetry device according to claim 1, further comprising means for correcting an effect of external light leaked from a contact part between said measured object and said measurement space dividing section.

5. The colorimetry device according to claim 4, wherein said effect on an output from said take-out port when said light source is turned on, is made to be corrected by using an output from said take-out port when said light source is turned off.

6. The colorimetry device according to claim 5, wherein said means comprises: first means for detecting an output from said take-out port when said light source is turned on; second means for detecting an output from said take-out port when said light source is turned off; and means for subtracting the output detected by said second means from the output detected by said first means.

* * * * *